United States Patent
Kitajima et al.

(10) Patent No.: US 10,434,041 B2
(45) Date of Patent: Oct. 8, 2019

(54) WATER-IN-OIL EMULSION COSMETIC COMPOSITION

(71) Applicant: SHISEIDO COMPANY, LTD., Tokyo (JP)

(72) Inventors: Masaki Kitajima, Yokohama (JP); Tomoko Sato, Yokohama (JP); Satoshi Yamaki, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 41 days.

(21) Appl. No.: 14/772,520

(22) PCT Filed: Mar. 6, 2014

(86) PCT No.: PCT/JP2014/055801
§ 371 (c)(1),
(2) Date: Oct. 14, 2015

(87) PCT Pub. No.: WO2014/136886
PCT Pub. Date: Sep. 12, 2014

(65) Prior Publication Data
US 2016/0058677 A1 Mar. 3, 2016

(30) Foreign Application Priority Data
Mar. 8, 2013 (JP) ................. 2013-046273

(51) Int. Cl.
| | | |
|---|---|---|
| *A61Q 19/00* | (2006.01) | |
| *A61K 8/92* | (2006.01) | |
| *A61K 8/06* | (2006.01) | |
| *A61K 8/25* | (2006.01) | |
| *A61K 8/31* | (2006.01) | |
| *A61K 8/37* | (2006.01) | |
| *A61Q 1/02* | (2006.01) | |
| *A61K 8/894* | (2006.01) | |
| *A61K 8/26* | (2006.01) | |
| *A61K 8/58* | (2006.01) | |
| *A61K 8/891* | (2006.01) | |

(52) U.S. Cl.
CPC ............ *A61K 8/062* (2013.01); *A61K 8/064* (2013.01); *A61K 8/25* (2013.01); *A61K 8/26* (2013.01); *A61K 8/31* (2013.01); *A61K 8/37* (2013.01); *A61K 8/58* (2013.01); *A61K 8/891* (2013.01); *A61K 8/894* (2013.01); *A61K 8/92* (2013.01); *A61Q 1/02* (2013.01); *A61Q 19/00* (2013.01)

(58) Field of Classification Search
CPC ...... A61Q 19/00; A61K 8/06; A61K 2800/48; A61K 8/92; A61K 2800/10; A61K 8/068
See application file for complete search history.

(56) References Cited

U.S. PATENT DOCUMENTS

| | | | |
|---|---|---|---|
| 4,164,564 A | 8/1979 | Chen | |
| 7,083,800 B1* | 8/2006 | Terren | A61K 8/064 424/401 |
| 8,815,958 B2 | 8/2014 | Sasaki | |
| 2009/0017081 A1* | 1/2009 | Takakura | A61K 8/064 424/401 |
| 2010/0011884 A1 | 5/2010 | Acker | |
| 2010/0172850 A1* | 7/2010 | Mitsui | A61K 8/06 424/59 |
| 2012/0134939 A1* | 5/2012 | Ueda | A61K 8/03 424/59 |
| 2012/0201905 A1* | 8/2012 | Mune | A61K 8/06 424/684 |
| 2012/0269748 A1* | 10/2012 | Tamura | A61K 8/042 424/59 |
| 2014/0148516 A1* | 5/2014 | Sasaki | A61K 8/26 514/785 |

FOREIGN PATENT DOCUMENTS

| | | | | |
|---|---|---|---|---|
| EP | 0719539 A2 * | 7/1996 | ............ | A61K 8/06 |
| JP | 10-120525 | 5/1998 | | |
| JP | 2003-504387 | 2/2003 | | |
| JP | 2004-224709 | 8/2004 | | |
| JP | 2009-137909 | 6/2009 | | |
| JP | 2012-67049 | 4/2012 | | |
| JP | WO 2012050024 A1 * | 4/2012 | ............ | A61K 8/26 |
| JP | 2012-102078 | 5/2012 | | |
| JP | 2012-116757 | 6/2012 | | |
| WO | WO-2013065664 A1 * | 5/2013 | ............ | A61Q 19/00 |

OTHER PUBLICATIONS

PCT/JP2014/055801 International Search Report dated May 27, 2014, 2 pages—English, 3 pages—Japanese.
U.S. Appl. No. 13/812,634, Notice of Allowance dated Apr. 256, 2019, 23 pages.
ICI Americas, Inc., "The HLB System: a time-saving guide to emulsifier selection" (1984), 22 pages, Year: 1984.
Society of Cosmetic Chemists, The HLB system, (Retrieved from internet URL:http://callscc.org/images/presentations/Mentor_2015_HLB.pdf], (Downloaded Apr. 24, 2019), 30 pages + 1 page citation information) (Year: 2019).
PCT/JP2014/055801 filed Mar. 6, 2014.
JP 2013-046273 filed Mar. 8, 2013.

* cited by examiner

*Primary Examiner* — Tracy Liu
(74) *Attorney, Agent, or Firm* — Andrew F. Young, Esq.; Lackenbach Siegel, LLP

(57) ABSTRACT

The present invention provides a water-in-oil type emulsion cosmetic composition with low viscosity while having excellent stability sufficient to withstand the inclusion of a polar oil. A water-in-oil type emulsion cosmetic composition of the present invention is characterized by comprising: (A) 0.1 to 2 mass % of an organically modified clay mineral; (B) 0.1 to 2 mass % of a hydrophobic silica; (C) 2 to 5 mass % of a silicone-type surfactant; (D) an oil component of which 10 to 50 mass % of the total oil component is a non-polar hydrocarbon oil; and (E) 20 to 60 mass % of a water phase component; wherein the (A) organically modified clay mineral and (B) hydrophobic silica total to 0.2 to 2 mass %; and a viscosity of the cosmetic composition as a whole is 1000 to 10000 mPa·s (30° C.; B type viscometer).

3 Claims, No Drawings

WATER-IN-OIL EMULSION COSMETIC COMPOSITION

CROSS REFERENCE TO RELATED APPLICATIONS

This application relates to and claims priority as a 371 national-phase from PCT/JP2014/055801 filed Mar. 6, 2014, the entire contents of which are incorporated herein by reference, which claims priority from JP Ser. No.: 2013-046273 filed on Mar. 8, 2013.

FIGURE SELECTED FOR PUBLICATION

None

TECHNICAL FIELD

The present invention relates to a water-in-oil type emulsion cosmetic composition. More specifically, it relates to a water-in-oil type emulsion cosmetic composition having excellent stability and low viscosity, which does not need to be re-emulsified by shaking at the time of use.

BACKGROUND ART

Conventionally, water-in-oil type emulsion compositions having an oil phase as an external phase and a water phase as an internal phase are a type of formulation that is suitable for use as formulations for external application to the skin due to their ability to effectively spread oil-soluble active ingredients, such as emollient oils, oil-soluble medicinal agents and UV absorbing agents over the skin, and are widely used in the cosmetic field, such as in skin care creams, milky lotions, and hair care creams.

However, water-in-oil type emulsion cosmetic compositions are often stabilized by gelling the oils constituting the external phase so as to immobilize water droplets and lower the collision frequency of the particles, thus requiring the viscosity to be raised. For this reason, it was considered to be difficult to achieve both low viscosity and stability in water-in-oil type emulsion cosmetic compositions, and it was difficult to simultaneously improve the stability over time and the spreadability and sensation of use at the time of application.

Various attempts have been made until now toward achieving water-in-oil type emulsion cosmetic compositions with low viscosity and stability. For example, Patent Document 1 proposes the use of a mixed powder combining highly oil-absorbent powders which are powders of different particle sizes (in other words, a powder mixture of a spherical organopolysiloxane elastomer powder and a hydrophobic silica powder) at a specific weight ratio, an oil part comprising 30 wt % or more of a silicone oil, and an organically modified clay mineral as an auxiliary emulsifier. Additionally, Patent Document 2 proposes the use of a specific hydrophobized silica as an emulsion stabilizer, and the use of a specific silicone surfactant as an emulsifier to improve the stability over time of the emulsion state, the feel and the texture.

However, in conventional low-viscosity water-in-oil type emulsion cosmetic compositions as mentioned above, there is a tendency for the amount of surfactant distributed to the oil phase to increase, making emulsification difficult, and resulting in a substantial loss of stability. Additionally, while polar oils have the action of stably dissolving various medicinal agents such as UV absorbing agents that have low solubility in non-polar oils, there are restrictions on the medicinal agents and the like that can be blended in low-viscosity water-in-oil type emulsion cosmetic compositions that cannot easily be provided with a high polar oil content. As a result, in order to obtain high SPF effects, for example, they must be made in a two-layer separated type in which the oil phase and the water phase are separated during storage, thus being inferior in terms of handling and the like.

RELATED ART

Patent Documents

Patent Document 1: JP 3474720 B
Patent Document 2: JP 3403223 B

SUMMARY OF THE INVENTION

Problems to be Solved by the Invention

The present invention was made in view of the drawbacks of the above-described conventional art, and has the purpose of offering a low-viscosity water-in-oil type emulsion cosmetic composition capable of maintaining excellent stability even when a polar oil is added.

Means for Solving the Problems

Upon performing diligent research, the present inventors discovered that a water-in-oil type emulsion cosmetic composition with low viscosity while having excellent stability sufficient to withstand the inclusion of a polar oil can be obtained by blending an organically modified clay mineral and a hydrophobic silica in specific amounts, and further blending an oil component containing a non-polar hydrocarbon oil in specific ratio, a silicone-type surfactant, and a water phase component in specific amounts, thereby achieving the present invention.

That is, the gist of the present invention is a water-in-oil type emulsion cosmetic composition comprising:
(A) 0.1 to 2 mass % of an organically modified clay mineral;
(B) 0.1 to 2 mass % of a hydrophobic silica;
(C) 2 to 5 mass % of a silicone-type surfactant;
(D) an oil component of which 10 to 50 mass % of the total oil component is a non-polar hydrocarbon oil; and
(E) 20 to 60 mass % of a water phase component;
wherein the (A) organically modified clay mineral and (13) hydrophobic silica total to 0.2 to 2 mass %; and
a viscosity of the cosmetic composition as a whole is 1000 to 10000 mPa·s (30° C.; B type viscometer).

Effects of the Invention

The water-in-oil type cosmetic composition according to the present invention has low viscosity and therefore is not sticky, is capable of providing a spreadable and fresh sensation of use, while simultaneously having good stability and therefore not requiring re-emulsification by shaking at the time of use, so it excels in ease of handling as well. Additionally, since a large quantity of polar oils can be added without sacrificing stability, medicinal agents that do not easily dissolve in non-polar oils can be stably dissolved. For this reason, the choice of medicinal agents that can be added increases, and a cosmetic composition with high medicinal effects can be obtained.

MODES FOR CARRYING OUT THE INVENTION

The water-in-oil type emulsion cosmetic composition of the present invention is characterized by essentially comprising (A) an organically modified clay mineral, (B) a hydrophobic silica, (C) a silicone-type surfactant, (D) an oil component, and (E) a water phase component.

<(A) Organically Modified Clay Mineral>

The (A) organically modified clay mineral used in the water-in-oil type emulsion cosmetic composition of the present invention is a type of colloidal hydrated aluminum silicate having a three-phase structure, generally obtained by modifying a clay mineral expressed by the following general formula (1) with a quaternary ammonium salt-type cationic surfactant:

$$(X,Y)_{2-3}(Si,Al)_4O_{10}(OH)_2Z_{1/3} \cdot nH_2O \tag{1}$$

where X=Al, Fe(III), Mn(III), Cr(III), Y=Mg, Fe(II), Ni, Zn, Li, Z=K, Na, Ca.

Specifically, it can be obtained by treating a clay mineral, such as a naturally occurring or synthetic (in this case, one wherein the (OH) group in the formula is substituted with a fluorine) substance in the montmorillonite group such as montmorillonite, saponite or hectorite (commercially available products of which include Veegum, Kunipia, and Laponite) or a synthetic mica known by the name of sodium silicic mica or sodium or lithium taeniolite (commercially available products of which include Dimonite from Topy Industries, Ltd.), with a quaternary ammonium salt-type cationic surfactant.

The quaternary ammonium salt-type cationic surfactant used here is represented by the following general formula (2):

where $R^1$ represents a benzyl group or an alkyl group having 10 to 22 carbon atoms, $R^2$ represents an alkyl group having 10 to 22 carbon atoms or a methyl group, $R^3$ and $R^4$ represent a hydroxyalkyl group or an alkyl group having 1 to 3 carbon atoms, and X represents a halogen atom or a methylsulfate residue.

Examples of this quaternary ammonium salt-type cationic surfactant include dodecyltrimethylammonium chloride, myristyltrimethylammonium chloride, cetyltrimethylammonium chloride, stearyltrimethylammonium chloride, aralkyltrimethylammonium chloride, behenyltrimethylammonium chloride, myristyldimethylethylammonium chloride, cetyldimethylethylammonium chloride, stearyldimethylethylammonium chloride, aralkyldimethylethylammonium chloride, behenyldimethylethylammonium chloride, myristyldiethylmethylammonium chloride, cetyldiethylmethylammonium chloride, stearyldiethylmethylammonium chloride, aralkyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, dibchenyldihydroxyethylammonium chloride, and corresponding bromides, as well as dipalmitylpropylethylammonium methylsulfate and the like. In carrying out the present invention, one or two or more of these may be chosen as needed.

Representative of organically modified clay minerals are dimethylalkylammonium hectorite, benzyldimethylstearylammonium hectorite and distearlydimethylammonium chloride-treated aluminum magnesium silicate and the like. As commercially available products, Bentone 27 (benzyldimethylstearylammonium chloride-treated hectorite; product of the National Lead Company) and Bentone 38 (distearyldimethylammonium chloride-treated hectorite; product of the National Lead Company) are preferred.

(A) The amount of the organically modified clay mineral to be blended should be 0.1 to 2 mass % with respect to the entire water-in-oil type emulsion cosmetic composition, more preferably 02 to 1.5 mass %, and even more preferably 0.4 to 1 mass %. If the amount of the (A) organically modified clay mineral is less than 0.1 mass %, then sufficient stability cannot be obtained, whereas if it is added in excess of 2 mass %, then the viscosity becomes high and there are problems in terms of texture such as the composition not being able to be taken up by the fingers or becoming heavy when trying to spread it over the skin.

<(B) Hydrophobic Silica>

The (B) hydrophobic silica used in the water-in-oil type emulsion cosmetic composition of the present invention is silica, i.e. silicic anhydride, wherein the silanol groups (hydroxyl groups) on the surface are subjected to a dimethyldichlorosilane treatment, an octylsilane treatment, a hexamethyldisilazane treatment, a dimethylsilicone oil treatment or a methacryloxysilane treatment. Of these, those that are subjected to a dimethyldichlorosilane treatment, an octylsilane treatment, a hexamethyldisilazane treatment or a diemthylsilicone oil treatment are preferable for having excellent cosmetic composition stability improving effects.

Additionally, portions of the (B) hydrophobic silica form three-dimensional structures with each other to form gel structures in the water-in-oil type emulsion cosmetic composition, which are believed to aid in stabilization. For this reason, those with a fine primary particle size of 5 to 20 nm which tend to form gel structures are preferred.

Examples of commercially available (B) hydrophobic silica products that satisfy the above conditions include the dimethyldichlorosilane-treated products AEROSIL R972, R972V, R972CF, 8974, R976 and R976S (products of Nippon Aerosil), the octylsilane-treated product AEROSIL R805 (product of Nippon Aerosil), the hexamethyldisilazane-treated products AEROSIL 8812, R812S and RX200 (products of Nippon Aerosil), and the dimethylsilicone oil-treated products AEROSIL R202 and RY200 (products of Nippon Aerosil). In the present invention, one or two or more of these can be added and used.

In the present invention, the blended amount of the (B) hydrophobic silica should be 0.1 to 2 mass % with respect to the entire water-in-oil type emulsion cosmetic composition, more preferably 0.5 to 1 mass % if the amount of (B) hydrophobic silica is less than 0.1 mass % with respect to the cosmetic composition, then sufficient stability cannot be obtained, and if the amount exceeds 2 mass %, a tendency to adversely affect the texture is observed, such as the occurrence of squeakiness.

The total amount of the (A) organically modified clay mineral and (B) hydrophobic silica in the water-in-oil type emulsion cosmetic composition of the present invention should be 0.2 to 2 mass % with respect to the entire water-in-oil type emulsion cosmetic composition, more preferably 0.5 to 1.5 mass %. If the total amount of the (A) organically modified clay mineral and (B) hydrophobic silica is less than 0.2 mass %, then sufficient stability may not be obtained and separation may occur, and if they are added in excess of 2 mass %, the viscosity becomes high and there is a tendency toward a degraded sensation of use.

<(C) Silicone Type Surfactant>

The (C) silicone type surfactant used in the present invention has an organopolysiloxane backbone, and has a polyoxyalkylene group and an alkyl group having two or more carbon atoms on a side chain. For example, a poly(oxyethylene/oxypropylene) methylpolysiloxane copolymer or an alkyl chain/silicone chain branched polyoxyethylene methylpolysiloxane copolymer or the like can be used.

Examples of commercially available products that can be favorably used include KF-6038 (product of Shin-Etsu Chemical Company) which is a lauryl PEG-9 polydimethylsiloxyethyl dimethicone, ABILEM 90 (product of Evonik Industries) which is a methylpolysiloxaneketylmethylpolysiloxane/poly(oxyethylene/oxypropylene) methylpolysiloxane copolymer, and 5200 Formulation aid (product of Toray Dow Corning) which is a lauryl PEG/PPG-18/18 dimethicone. In the present invention, one or two or more of these can be added and used.

In the present invention, the blended amount of (C) silicone type surfactant should be 2 to 5 mass % with respect to the entire water-in-oil type emulsion cosmetic composition, more preferably 2.5 to 4.5 mass %, and even more preferably 3 to 4 mass %. If the blended amount is less than 2 mass %, then the viscosity becomes high and the sensation of use tends to become worse, while on the other hand, if the amount exceeds 5 mass %, there is a tendency for the stability to be lost, and separation may occur.

<(D) Oil Component>

The (D) oil component used in the water-in-oil type emulsion cosmetic composition of the present invention contains a non-polar hydrocarbon oil in an amount of 10 to 50 mass % with respect to the total oil content. If the proportion of the non-polar hydrocarbon oil in the total oil content lies outside said range, then the stability can be reduced, and separation may occur.

As the non-polar hydrocarbon oil in the present invention, a hydrocarbon oil that is generally known as a non-polar oil or low-polarity oil can be used. Examples of non-polar hydrocarbon oils include liquid paraffin, isohexadecane, isododecane, ozokerite, squalane, squalene, pristane, paraffin, isoparaffin, ceresin, vaseline, microcrystalline wax, and hydrogenated polyisobutene.

On the other hand, as the oil components other than the non-polar hydrocarbon oil contained in the (D) oil component, any component chosen from among oils and fats, waxes, higher fatty acids, higher alcohols, ester oils and silicone oils can be added, and there are no particular restrictions as long as the effects of the present invention are not lost.

In particular, a polar oil may be added to the present invention. The amount of polar oil blended should be 90 mass % or less with respect to the total oil content, preferably 70 mass % or les, and more preferably 50 mass % or less. If the amount of polar oil added exceeds 90 mass % with respect to the total oil content, the stability may be reduced. On the other hand, while there is no particular restriction on the lower limit of the amount of the polar oil added, when considering the sensation of use and the stability when dissolving a medicinal agent, it should preferably be at least 20 mass % with respect to the total oil content, and more preferably at least 30 mass %.

Examples of polar oils are oil components having an 10B value of 0.05 to 0.80, such as isostearic acid, isopropyl myristate, cetyl octanoate, octyldodecyl myristate, isopropyl palmitate, butyl stearate, hexyl laurate, myristyl myristate, decyl oleate, hexyldecyl dimethyloctanoate, isononyl isononanoate, cetyl lactate, myristyl lactate, lanolin acetate, isocetyl stearate, isocetyl isostearate, cetyl ethylhexanoate, cholesteryl 12-hydroxystearate, ethylene glycol di-2-ethylhexanoate, dipentaerythritol fatty acid ester, N-alkylglycol monoisostearate, neopentylglycol dicaprate, diisostearyl malate, glycerin di-2-heptylundecanoate, trimethylolpropane tri-2-ethylhexanoate, trimethylolpropane triisostearate, pentaerythritol tetra-2-ethylhexanoate, glyceryl tri-2-ethylhexanoate (triethylhexanoin), trimethylolpropane triisostearate, cetyl isooctanoate, cetyl 2-ethylhexanoate, 2-ethylhexyl palmitate, ($C_{12-15}$)alkyl benzoate, cetearyl isononanoate, glycerin tri(caprylate/caprate), butylene glycol (dicaprylate/caprate), glycerin trimyristate, tri-2-heptylundecanoic acid glyceride, castor oil fatty acid methyl esters, oleyl oleate, cetostearyl alcohol, acetoglyceride, 2-heptylundecyl palmitate, diisobutyl adipate, N-lauroyl-L-glutamic acid 2-octydodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di-2-ethylhexyl succinate, ethyl acetate, butyl acetate, amyl acetate, triethyl citrate, 2-ethylhexyl paramethoxycinnamate, tripropylene glycol dipivalate, and 2-ethylhexyl 2-cyano-3,3-diphenylacrylate.

<(E) Water Phase Component>

The (E) water phase component used in the water-in-oil type emulsion cosmetic composition of the present invention may contain water (ion exchanged water, purified water, natural water etc.) or an aqueous solvent, as well as those components that can normally be used in cosmetic compositions, within a range not sacrificing the stability of the cosmetic composition.

Typically, a lower alcohol or polyhydric alcohol may be added.

Examples of lower alcohols include ethanol, methanol, propanol, isopropanol, butanol, isobutanol and t-butanol.

Examples of polyhydric alcohols include dihydric alcohols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol); trihydric alcohols (e.g., glycerin and trimethylol propane); tetrahydric alcohols (e.g., pentaerythritols such as 1,2,6-hexanetriol); pentahydric alcohols (e.g., xylitol); hexahydric alcohols (e.g., sorbitol and mannitol); polyhydric alcohol polymers (e.g., diethylene glycol, dipropylene glycol, triethylene glycol, polypropylene glycol, tetraethylene glycol, diglycerin, polyethylene glycol, triglycerin, tetraglycerin and polyglycerin); dihydric alcohol alkyl ethers (e.g., ethylene glycol monomethyl ether, ethylene glycol monoethyl ether, ethylene glycol monobutyl ether, ethylene glycol monophenyl ether (phenoxy ethanol), ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutyl ether); alkyl ethers of dihydric alcohols (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether); dihydric alcohol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate); glycerin monoalkyl ethers (e.g., chimyl alcohol, selachyl alcohol and batyl alcohol); sugar alcohols (e.g., sorbitol, maltitol, maltotriose, mannitol, sucrose, erythritol, glucose, fructose, starch-degraded sugars, maltose, xylitose and starch-degraded sugar-reduced alcohols); glysolid; tetrahydrofurfuryl alcohol; POE-tetrahydrofurfuryl alcohol, POP-butyl ether; POP/POE-butyl ether; tripolyoxypropylene glyceryl ether; POP-glyceryl ether; POP-glyceryl ether phosphate; POP/POE-pentaerythritol ether, polyglycerin, etc.

The blended amount of the (E) water phase component in the present invention, in other words, the internal water phase amount of the water-in-oil type emulsion cosmetic composition, is 20 to 60 mass %, preferably 30 to 50 mass %, and more preferably 35 to 45 mass %. If the amount of the water phase component is less than 20 mass %, sufficient stability cannot be obtained and separation may occur. On the other hand, if it is added in excess of 60 mass %, the viscosity tends to become too high, and the sensation of use may become worse.

Additionally, the water-in-oil type emulsion cosmetic composition of the present invention is in the form of a low-viscosity emulsion with a viscosity of 1000 to 10000 mPa·s (30° C., B-type viscometer). If the viscosity is less than 1000 mPa·s, then it tends to become more difficult to obtain sufficient stability, and on the other hand, if the viscosity exceeds 10000 mPa·s, the viscosity becomes too high, and the composition becomes heavy to spread at the time of application, so a good sensation of use cannot be obtained.

The water-in-oil type emulsion cosmetic composition of the present invention may include, as needed, other optional additive ingredients that are normally used in cosmetics, within a range not detracting from the effects of the present invention, e.g., surfactants, metal ion sequestering agents, powder components, sugars, amino acids, organic amines, pH adjusters, UV absorbing agents, skin nutrients, vitamins, antioxidants and fragrances.

In particular, the water-in-oil type emulsion cosmetic composition of the present invention can contain large quantities of polar oils, so even UV absorbing agents that do not easily dissolve in non-polar oils can be stably added. The UV absorbing agents that can be added include, for example, cinnamic acid derivatives such as ethylhexyl methoxycinnamate (octylmethoxycinnamate), isopropyl methoxycinnamate and isoamyl methoxycinnamate; para-aminobenzoic acid (hereinafter abbreviated to "PABA") derivatives such as PABA, ethyl PABA, ethyl-dihydroxypropyl PABA, ethylhexyl-dimethyl PABA and glyceryl PABA; salicylic acid derivatives such as homosalate, ethylhexyl salicylate, dipropylene glycol salicylate, and TEA salicylate; benzophenone derivatives such as benzophenone-1, benzophenone-2, benzophenone-3 or oxybenzone, benzophenone-4, benzophenone-5, benzophenone-6, benzophenone-8, benzophenone-9 and benzophenone-12; benzylidene camphor derivatives such as 3-benzylidene camphor, 4-methylbenzylidene camphor and polyacrylamide methylbenzylidene camphor; triazine derivaties such as anisotriazine, ethylhexyl triazone, diethylhexyl butamido triazone, 2,4,5-tris(diisobutyl-4'-aminobenzalmalonate)-s-triazine, 2,4-bis-[{4-(2-ethylhexyloxy)-2-hydroxy}-pheny]-6-(4-methoxyphenyl)-1,3,5-triazine (bis-ethyihexyloxyphenol methoxyphenyl triazine); imidazole derivatives such as 4-imidazole acrylic acid ethyl ester and 5-methyl-2-phenylbenzoimidazole; phenylbenzotriazole derivatives such as drometrizole trisiloxane and methylene bis(benzotriazolyl tetramethylbutylphenol); anthranil derivatives such as menthyl anthranilate; imidazoline derivatives such as ethylhexyldimethoxybenzylidene dioxoimidazoline propionate; benzalmalonate derivatives such as polyorganosiloxanes having benzalmalonate functional groups; 4,4-diarylbutadiene derivatives such as 1,1-dicarboxy(2,2'-dimethylpropyl)-4,4-diphenylbutadiene; and 2-cyano-3,3-diphenylpropa-2-enic acid 2-ethylhexyl ester (octocrylene).

As other UV absorbing agents, water soluble UV absorbing agents having sulfonic acid groups such as phenylbenzimidazole-5-sulfonic acid and salts thereof, and phenylene-bis-benzimidazole-tetrasulfonic acid and salts thereof are also preferable. Basic compounds (neutralizing base) to be used for obtaining the salts include sodium hydroxide, potassium hydroxide, triethanolamine, 2-amino-2-methyl-1-propanol, 2-amino-2-methyl-1,3-propanediol and sodium N-methyltaurine.

The water-in-oil type emulsion cosmetic composition of the present invention can be prepared by a conventional method, and the method of emulsification is not particularly limited. For example, there is a method of respectively heating the water phase and the oil phase to about 70° C., gradually adding the heated water phase to the oil phase, emulsifying in an emulsifier, and then, cooling to room temperature, but the method is not limited thereto.

The water-in-oil type emulsion cosmetic composition according to the present invention can be applied to a wide range of cosmetics, examples of which include products such as sun care cosmetic compositions (sunscreens, sun oils, after-sun lotions, etc.), whitening beauty lotions, milky lotions, creams, makeup base, and emulsified foundations.

EXAMPLES

Herebelow, the present invention will be explained in further detail by describing examples, but the present invention is not to be construed as being limited by these examples. The blended amounts are expressed in mass % unless stated otherwise. Before the examples, the methods for evaluation used in the present invention shall be explained.

(1) Stability

The appearance of a sample stored for 1 month at room temperature (25° C.) was evaluated according to the following criteria:

A: No separation of water or oil was observed in the appearance.

B: Separation of water or oil was observed in the appearance within 1 month.

(2) Viscosity

A sample that was stored at 30° C. for 1 hour after production was measured using a B-type viscometer (BL-type, Rotor No. 3, 12 rpm). The measurement was not made when separation occurred.

Water-in-oil type emulsion cosmetic compositions (test samples) were prepared using the formulations shown in Tables 1-4 below, and evaluated for the respective properties in accordance with the above-described evaluation methods. The results are shown in Tables 1-4.

TABLE 1

|  | Sample 1-1 | Sample 1-2 | Sample 1-3 | Sample 1-4 | Sample 1-5 | Sample 1-6 | Sample 1-7 |
|---|---|---|---|---|---|---|---|
| (A) Dimethyldistearylammonium modified hectorite | 1 | 0.2 | 1 | 2 | 0.5 | 0 | 2 |
| (B) Silylated silicic anhydride | 0.5 | 0.8 | 1 | 0.5 | 2 | 2 | 0 |
| (C) Lauryl PEG-9 polydimethyl siloxyethyl dimethicone | 3 | 3 | 3 | 3 | 3 | 3 | 3 |
| (D) Isohexadecane | 25 | 25 | 25 | 25 | 25 | 25 | 25 |
| Pentaerythritol tetra-2-ethylhexanoate | 25 | 25 | 25 | 25 | 25 | 25 | 25 |
| Dimethicone | 10 | 10 | 10 | 10 | 10 | 10 | 10 |
| (E) Ion-exchanged water | 25 | 25.5 | 24.5 | 24 | 24 | 24.5 | 24.5 |
| Glycerin | 5 | 5 | 5 | 5 | 5 | 5 | 5 |
| Alcohol | 5 | 5 | 5 | 5 | 5 | 5 | 5 |
| Salt | 0.5 | 0.5 | 0.5 | 0.5 | 0.5 | 0.5 | 0.5 |
| TOTAL | 100 | 100 | 100 | 100 | 100 | 100 | 100 |
| (A) + (B) Amount | 1.5 | 1 | 2 | 2.5 | 2.5 | 2 | 2 |
| Non-polar hydrocarbon oil content/ total oil content (%) | 41.7 | 41.7 | 41.7 | 41.7 | 41.7 | 41.7 | 41.7 |
| Internal water phase content (%) | 35.5 | 36.0 | 35.0 | 34.5 | 34.5 | 35.0 | 35.0 |
| Evaluation Stability | A | A | A | A | A | B | B |
| Viscosity* | 3,200 | 1,200 | 4,800 | 12,200 | 15,400 | — | — |

*"—" indicates that separation occurred.

As shown in Table 1, when containing the (A) organically modified clay mineral and (B) hydrophobic silica respectively in the range of 0.1 to 2 mass %, and when their total ("(A)+(B) Amount") was 0.2 to 2 mass % with respect to the entire cosmetic composition, both a low viscosity of 10000 mPa·s or less and excellent stability were achieved despite containing a polar oil (pentaerythritol tetra-2-ethylhexanoate) (Sample 1-1, Sample 1-2, Sample 1-3). On the other hand, when the respective amounts and total amount of the (A) organically modified clay mineral and (B) hydrophobic silica are outside the above-described ranges, separation over time (Sample 1-6, Sample 1-7) and high viscosity (Sample 1-4, Sample 1-5) were observed.

TABLE 2

|  | Sample 1-1 | Sample 2-1 | Sample 2-2 | Sample 2-3 | Sample 2-4 |
|---|---|---|---|---|---|
| (A) Dimethyldistearylammonium modified hectorite | 1 | 1 | 1 | 1 | 1 |
| (B) Silylated silicic anhydride | 0.5 | 0.5 | 0.5 | 0.5 | 0.5 |
| (C) Lauryl PEG-9 polydimethyl siloxyethyl dimethicone | 3 | 2 | 5 | 1 | 6 |
| (D) Isohexadecane | 25 | 25 | 25 | 25 | 25 |
| Pentaerythritol tetra-2-ethylhexanoate | 25 | 25 | 25 | 25 | 25 |
| Dimethicone | 10 | 10 | 10 | 10 | 10 |
| (E) Ion-exchanged water | 25 | 26 | 23 | 27 | 22 |
| Glycerin | 5 | 5 | 5 | 5 | 5 |
| Alcohol | 5 | 5 | 5 | 5 | 5 |
| Salt | 0.5 | 0.5 | 0.5 | 0.5 | 0.5 |
| TOTAL | 100 | 100 | 100 | 100 | 100 |
| (A) + (B) Amount | 1.5 | 1.5 | 1.5 | 1.5 | 1.5 |
| Non-polar hydrocarbon oil content/ total oil content (%) | 41.7 | 41.7 | 41.7 | 41.7 | 41.7 |
| Internal water phase content (%) | 35.5 | 36.5 | 33.5 | 37.5 | 32.5 |
| Evaluation Stability | A | A | A | A | B |
| Viscosity* | 3,200 | 8,800 | 1,500 | 13,200 | — |

*"—" indicates that separation occurred.

As shown in Table 2, when the amount of (C) silicone-type surfactant was in the range of 2 to 5 mass % with respect to the entire cosmetic composition, excellent stability was able to be achieved even with a low viscosity (Sample 1-1, Sample 2-1, Sample 2-2). On the other hand, when the amount of the (C) silicone-type surfactant was outside the above-mentioned range, high viscosity (Sample 2-3) and separation over time (Sample 2-4) were observed.

TABLE 3

|  | Sample 1-1 | Sample 3-1 | Sample 3-2 | Sample 3-3 | Sample 3-4 |
|---|---|---|---|---|---|
| (A) Dimethyl distearylammoninm modified hectorite | 1 | 1 | 1 | 1 | 1 |
| (B) Silylated silicic anhydride | 0.5 | 0.5 | 0.5 | 0.5 | 0.5 |
| (C) Lauryl PEG-9 polydimethyl siloxyethyl dimethicone | 3 | 3 | 3 | 3 | 3 |
| (D) Isohexadecane | 25 | 20 | 30 | 5 | 35 |
| Pentaerythritol tetra-2-ethylhexanoate | 25 | 30 | 20 | 45 | 15 |
| Dimethicone | 10 | 10 | 10 | 10 | 10 |
| (E) Ion-exchanged water | 25 | 25 | 25 | 25 | 25 |
| Glycerin | 5 | 5 | 5 | 5 | 5 |
| Alcohol | 5 | 5 | 5 | 5 | 5 |
| Salt | 0.5 | 0.5 | 0.5 | 0.5 | 0.5 |
| TOTAL | 100 | 100 | 100 | 100 | 100 |
| (A) + (B) Amount | 1.5 | 1.5 | 1.5 | 1.5 | 1.5 |
| Non-polar hydrocarbon oil content/ total oil content (%) | 41.7 | 33.3 | 50.0 | 8.3 | 58.3 |
| Internal water phase content (%) | 35.5 | 35.5 | 35.5 | 35.5 | 35.5 |
| Evaluation Stability | A | A | A | B | B |
| Viscosity* | 3,200 | 3,500 | 2,400 | — | — |

*"—" indicates that separation occurred.

As shown in Table 3, when non-polar hydrocarbon oils (isohexadecane) account for 10 to 50 mass % of the total oil content in the (D) oil component, excellent stability was achieved while having low viscosity (Sample 1-1, Sample 3-1, Sample 3-2). On the other hand, when the proportion of non-polar hydrocarbon oil in the (D) oil component was outside the above-described range, separation over time was observed (Sample 3-3, Sample 3-4).

TABLE 4

|  | Sample 1-1 | Sample 4-1 | Sample 4-2 | Sample 4-3 | Sample 4-4 |
|---|---|---|---|---|---|
| (A) Dimethyldistearylammonium modified hectorite | 1 | 1 | 1 | 1 | 1 |
| (B) Silylated silicic anhydride | 0.5 | 0.5 | 0.5 | 0.5 | 0.5 |
| (C) Lauryl PEG-9 polydimethyl siloxyethyl dimethicone | 3 | 3 | 3 | 3 | 3 |
| (D) Isohexadecane | 25 | 27 | 18 | 33 | 12 |
| Pentaerythritol tetra-2-ethylhexanoate | 25 | 27 | 18 | 33 | 12 |
| Dimethicone | 10 | 10 | 10 | 10 | 10 |
| (E) Ion-exchanged water | 25 | 21 | 39 | 9 | 51 |
| Glycerin | 5 | 5 | 5 | 5 | 5 |
| Alcohol | 5 | 5 | 5 | 5 | 5 |
| Salt | 0.5 | 0.5 | 0.5 | 0.5 | 0.5 |
| TOTAL | 100 | 100 | 100 | 100 | 100 |
| (A) + (B) Amount | 1.5 | 1.5 | 1.5 | 1.5 | 1.5 |
| Non-polar hydrocarbon oil content/ total oil content (%) | 41.7 | 42.2 | 39.1 | 43.4 | 35.3 |
| Internal water phase content (%) | 35.5 | 31.5 | 49.5 | 19.5 | 61.5 |
| Evaluation Stability | A | A | A | B | A |
| Viscosity* | 3,200 | 3,500 | 9,200 | — | 19,700 |

*"—" indicates that separation occurred.

As shown in Table 4, when the amount of (E) the water phase component was in the range of 20 to 60 mass % with respect to the entire cosmetic composition, excellent stability was achieved while having low viscosity (Sample 1-1, Sample 4-1, Sample 4-2). On the other hand, when the amount of the (E) water phase component was outside the above-mentioned range, separation over time (Sample 4-3) and high viscosity (Sample 4-4) were observed.

Formulation Examples

Herebelow, formulation examples of the water-in-oil type emulsion cosmetic composition of the present invention will be given. Needless to say, the present invention is not in any way limited by these formulation examples, and is defined by the scope of the claims. All amounts are indicated as mass % with respect to the entire product.

Formulation Example 1 (Milky Lotion)

| (Ingredient) | Content (%) |
|---|---|
| (1) Water | 25 |
| (2) Glycerin | 5 |

| (Ingredient) | Content (%) |
|---|---|
| (3) Ethanol | 5 |
| (4) Sodium chloride | 0.5 |
| (5) Disteardimonium hectorite | 1 |
| (6) Silylated silicic anhydride | 0.5 |
| (7) Lauryl PEG-9 polydimethylsiloxyethyl dimethicone | 3 |
| (8) Isohexadecane | 25 |
| (9) Pentaerythritol tetra-2-ethylhexanoate | 25 |
| (10) Dimethicone | 10 |

Production Method:

(5) to (10) were mixed and homogeneously dispersed (oil phase). On the other hand, (1) to (4) were homogeneously mixed (water phase). The water phase was gradually added to the oil phase, homogeneously dispersed with a homodisper, then the emulsion particles were adjusted to produce a low-viscosity water-in-oil type emulsion.

Formulation Example 2 (Foundation Primer)

| (Ingredient) | Content (%) |
|---|---|
| (1) Water | 25 |
| (2) 1,3-butylene glycol | 5 |
| (3) Ethanol | 5 |
| (4) Sodium chloride | 0.5 |
| (5) Disteardimonium hectorite | 1 |
| (6) Silylated silicic anhydride | 0.5 |
| (7) Lauryl PEG-9 polydimethylsiloxyethyl dimethicone | 3 |
| (8) Isohexadecane | 15 |
| (9) Pentaerythritol tetra-2-ethylhexanoate | 5 |
| (10) Dimethicone | 20 |
| (11) Polymethylsilsesquioxane | 15 |
| (12) Microparticulate titanium oxide | 2 |
| (13) Crosslinked silicone powder | 3 |

Production Method (5) to (13) were mixed and homogeneously dispersed (oil phase). On the other hand, (1) to (4) were homogeneously mixed (water phase). The water phase was gradually added to the oil phase, homogeneously dispersed with a homodisper, then the emulsion particles were adjusted to produce a low-viscosity water-in-oil type emulsion.

Formulation Example 3 (Emulsion Foundation)

| (Ingredient) | Content (%) |
|---|---|
| (1) Water | 25 |
| (2) Glycerin | 5 |
| (3) Ethanol | 5 |
| (4) Sodium chloride | 0.5 |
| (5) Disteardimonium hectorite | 1 |
| (6) Silylated silicic anhydride | 0.5 |
| (7) Lauryl PEG-9 polydimethylsiloxyethyl dimethicone | 3 |
| (8) Isohexadecane | 20 |
| (9) Pentaerythritol tetra-2-ethylhexanoate | 18 |
| (10) Dimethicone | 10 |
| (11) Ethylhexyl methoxycinnamate | 2 |
| (12) Hydrophobicized powder | 5 |
| (13) Microparticulate titanium oxide | 5 |

Production Method (5) to (13) were mixed and homogeneously dispersed (oil phase). On the other hand, (1) to (4) were homogeneously mixed (water phase). The water phase was gradually added to the oil phase, homogeneously dispersed with a homodisper, then the emulsion particles were adjusted to produce a low-viscosity water-in-oil type emulsion.

The invention claimed is:

1. A water-in-oil emulsion cosmetic composition comprising:
   (A) 0.1 to 1.5 mass % of dimethyldistearylammonium modified hectorite;
   (B) 0.1 to 1 mass % of a silylated silicic anhydride;
   (C) 2 to 5 mass % of a silicone surfactant;
   (D) an oil component of which 10 to 50 mass % of the total oil component is a non-polar hydrocarbon oil; and
   (E) 20 to 60 mass % of a water phase;
   wherein the (A) dimethyldistearylammonium modified hectorite and (B) silylated silicic anhydride total to 0.2 to 2 mass %;
   the (A) dimethyldistearylammonium modified hectorite is dispersible in the oil component;
   a viscosity of the cosmetic composition as a whole is 1000 to 10000 mPa·s (30° C.; B type viscometer);
   the (D) oil component comprises a silicone oil; and
   wherein the composition exhibits no phase separation when stored for 1-month at room 25° C.

2. A water-in-oil emulsion cosmetic composition according to claim 1, wherein the (D) oil component comprises a polar oil.

3. A water-in-oil emulsion cosmetic composition according to claim 2, wherein the (D) oil component contains the polar oil in a range of 20 to 90 mass % with respect to the entire oil component.

* * * * *